(12) United States Patent
Ochoa

(10) Patent No.: US 8,048,173 B2
(45) Date of Patent: Nov. 1, 2011

(54) PROSTHETIC FOOT

(75) Inventor: Adam A. Ochoa, Tempe, AZ (US)

(73) Assignee: Ability Dynamics, L.L.C., Scottsdale, AZ (US)

( * ) Notice: Subject to any disclaimer, the term of this patent is extended or adjusted under 35 U.S.C. 154(b) by 387 days.

(21) Appl. No.: 11/901,845

(22) Filed: Sep. 19, 2007

(65) Prior Publication Data

US 2009/0076626 A1    Mar. 19, 2009

(51) Int. Cl.
*A61F 2/68* (2006.01)
*A61F 2/66* (2006.01)

(52) U.S. Cl. .................. 623/55; 623/53; 623/54

(58) Field of Classification Search ............... 623/53–56
See application file for complete search history.

(56) References Cited

U.S. PATENT DOCUMENTS

| | | | | |
|---|---|---|---|---|
| 5,376,139 A | * | 12/1994 | Pitkin | 623/51 |
| 5,507,838 A | * | 4/1996 | Chen | 623/55 |
| 5,549,714 A | * | 8/1996 | Phillips | 623/33 |
| 5,653,767 A | * | 8/1997 | Allen et al. | 623/52 |
| 5,888,214 A | | 3/1999 | Ochoa | |
| 6,099,572 A | * | 8/2000 | Mosler et al. | 623/53 |
| 6,767,370 B1 | * | 7/2004 | Mosler et al. | 623/55 |
| 6,797,009 B1 | * | 9/2004 | Laghi | 623/53 |
| 6,875,241 B2 | * | 4/2005 | Christesen | 623/56 |
| 2004/0153168 A1 | | 8/2004 | Childress et al. | |
| 2010/0004757 A1 | | 1/2010 | Clausen et al. | |

* cited by examiner

*Primary Examiner* — David Isabella
*Assistant Examiner* — Jacqueline Woznicki
(74) *Attorney, Agent, or Firm* — Snell & Wilmer L.L.P.

(57) ABSTRACT

A prosthetic foot comprises a ground engaging bottom resilient member, a resilient heel member, and a resilient toe member that collectively circumscribe an open volumetric space. The members resilient compress to absorb compressive force throughout the entire stride of an individual utilizing the foot.

2 Claims, 8 Drawing Sheets

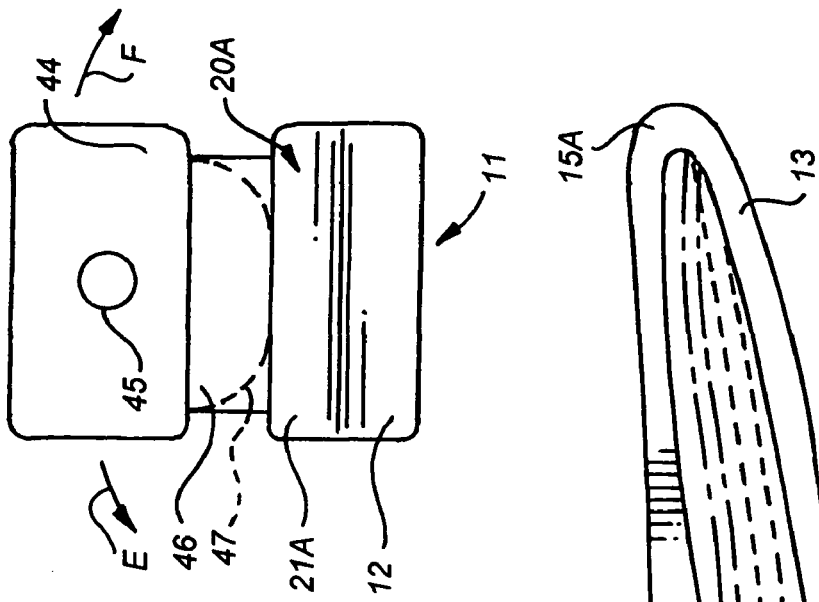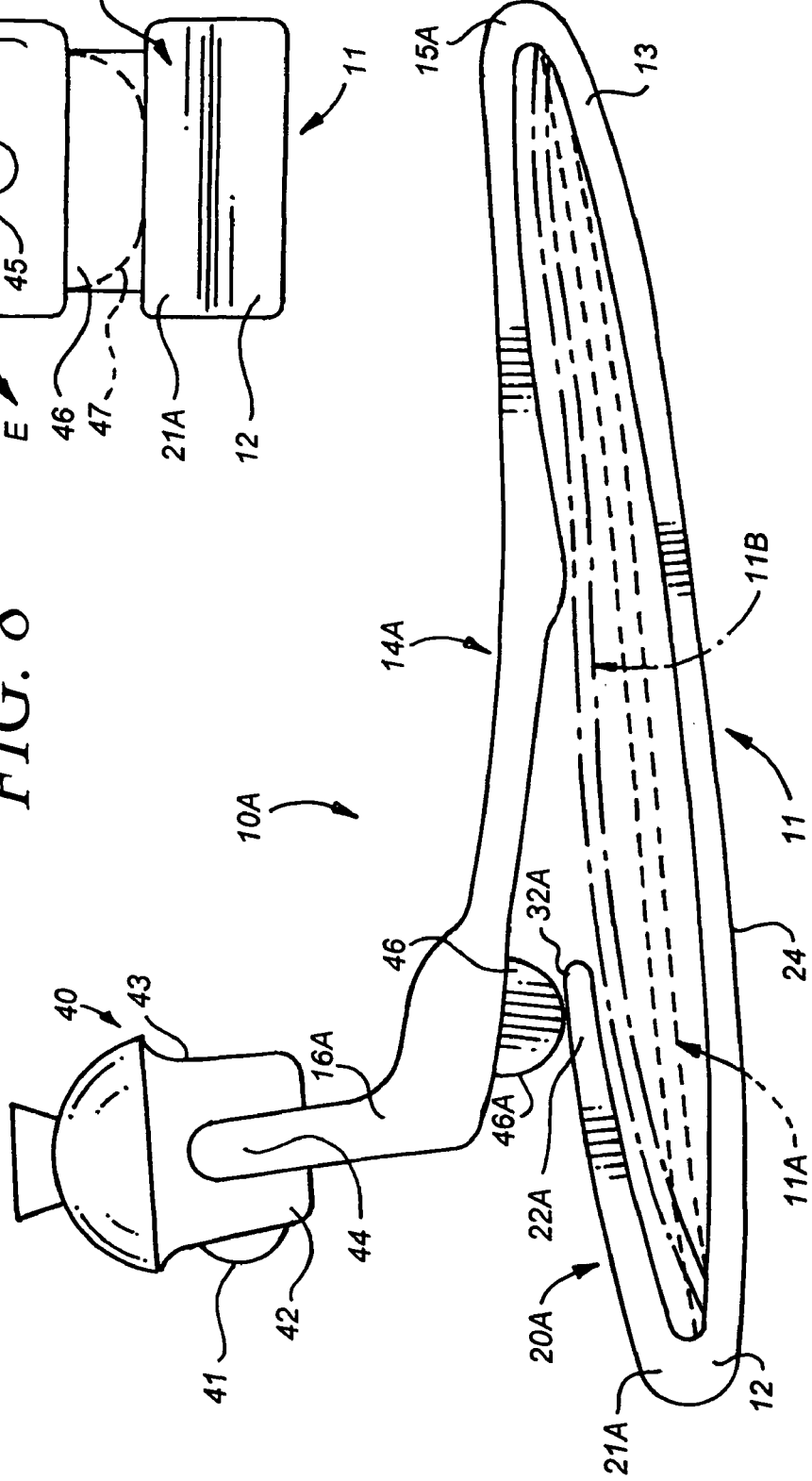

PROSTHETIC FOOT

This invention pertains to prosthetic devices.

More particularly, the invention pertains to a prosthetic foot that, when utilized by an amputee, better replicates the action of a real foot and reduces the risk of injury to the amputee.

Prosthetic feet are well known in the art. In use, such prosthetic feet typically do not replicate the action of a real foot and can generate "kickback" or "kickforward" reactions that increase the risk of injury to an amputee utilizing the foot.

Accordingly, it would be highly desirable to provide an improved prosthetic foot which would better replicate the action of a true foot.

Therefore, it is a principal object of the invention to provide an improved prosthetic foot.

A further object of the invention is to provide an improved prosthetic foot which minimizes or eliminates "kickback" forces when the foot is utilized to walk over a door jamb or other raised profile object on a floor or on the ground.

These and other, further and more specific objects and advantages of the invention will be apparent to those skilled in the art from the following detailed description thereof, taken in conjunction with the drawings, in which:

FIG. 7 is a side view illustrating alternate embodiments of the prosthetic foot of FIG. 1;

FIG. 8 is a back view further illustrating the prosthetic foot of FIG. 7;

Figure 1:
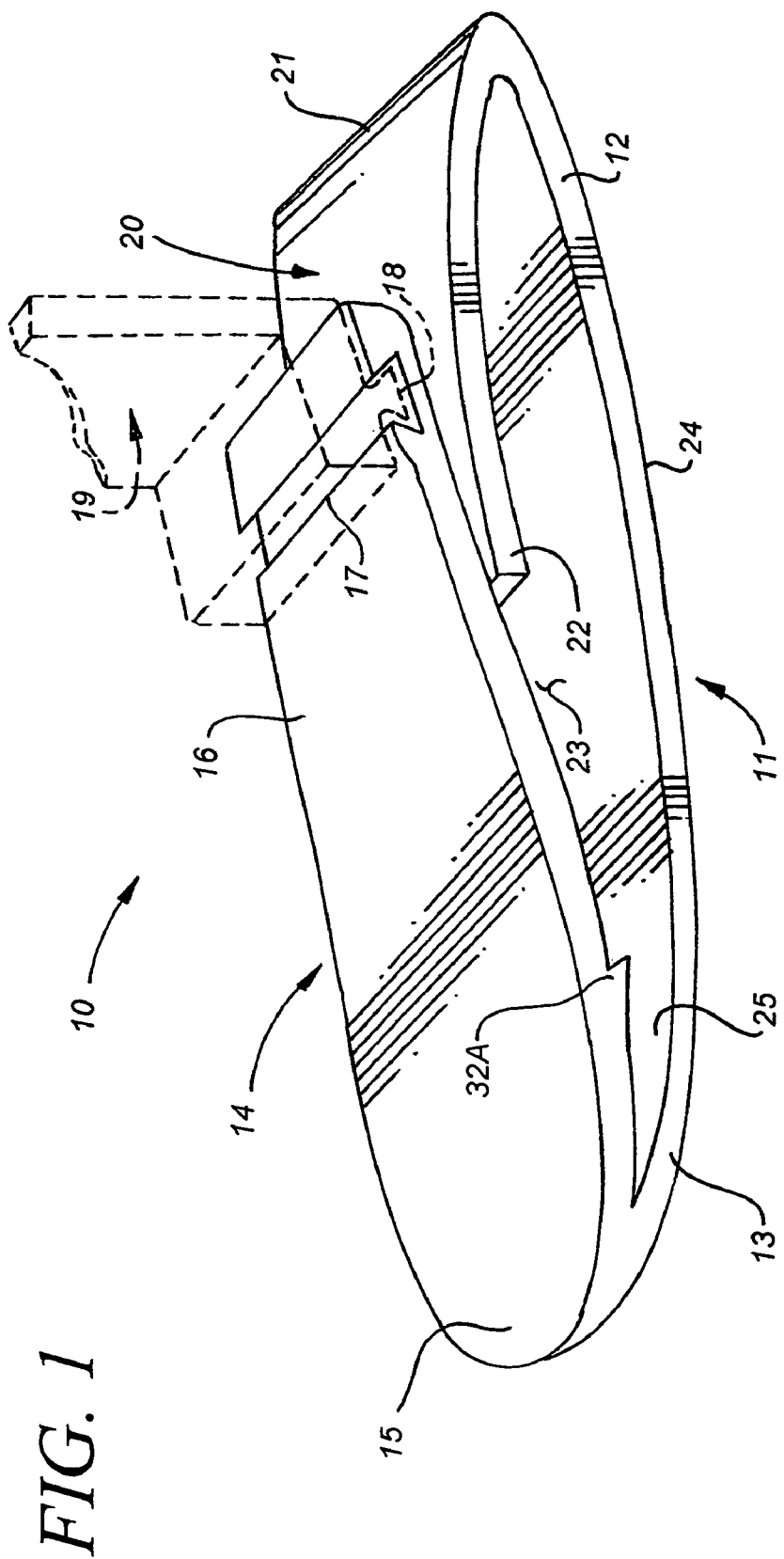
FIG. 1 is a perspective view illustrating a prosthetic foot constructed in accordance with the invention.

Briefly, in accordance with the invention, I provide an improved prosthetic foot. The foot comprises a ground engaging bottom resilient member having a front end and a back end and an intermediate section spanning between and connecting the front end and the back end; a heel resilient member having a rear end connected to the back end of the bottom resilient member, extending upwardly from the back end, and, having a forward end spaced apart from the rear end and the bottom resilient member; and, a toe resilient member having a proximate end connected to the front end of the bottom member, extending upwardly from the front end and over the forward end of the heel resilient member, and having a distal end spaced apart from the proximate end, from the front end, and above the heel resilient member. The bottom member, heel member, and toe member are shaped and dimensioned and have a resistance response to a compressive applied force such that when the compressive applied force compresses said prosthetic foot against the ground the intermediate section of the bottom member upwardly deflects from the ground, and the toe member downwardly deflects toward the ground and contacts the heel resilient member and deflects the heel member toward the ground and toward the bottom member.

In another embodiment of the invention, I provide a prosthetic foot. The foot includes a ground engaging bottom resilient member having a front end and a back end and an intermediate section spanning between and connecting the front end and the back end; a toe resilient member having a rear end connected to the front end of the bottom resilient member, extending upwardly from the front end, and, having a forward end spaced apart from the rear end and the bottom resilient member; and, a heel resilient member having a proximate end connected to the back end of the bottom member, extending upwardly from the back end and over the forward end of the toe resilient member, and having a distal end spaced apart from the proximate end, from the back end, and above the toe resilient member. The bottom member, heel member, and toe member are shaped and dimensioned and have a resistance response to a compressive applied force such that when the compressive applied force compresses the prosthetic foot against the ground the intermediate section of the bottom member upwardly deflects from the ground, and, the heel member downwardly deflects toward the ground and contacts the toe resilient member and deflects the toe member toward the ground and toward the bottom member.

Turning now to the drawings, which depict the presently preferred embodiments of the invention for the purpose of illustrating the practice thereof and not by way of limitation of the scope of the invention, and in which like reference characters refer to corresponding elements throughout the several views, FIGS. 1 to 6 illustrate one presently preferred embodiment of the prosthetic foot of the invention. The prosthetic foot is generally indicated by reference character 10.

In FIG. 1, foot 10 includes a first resilient flexion bottom member 11 with ends 12 and 13, a second resilient flexion heel member 20 with ends 21 and 22, and a third resilient flexion toe member 14 with ends 15 and 16. End 21 of member 20 is connected to end 12 of member 11. End 15 of member 14 is connected to end 13 of member 11. Members 11, 14, 20 can be fabricated together as a unitary member or the end pairs 21-12 and 13-15 can be connected with adhesive, bolts, or any other desired fastener or fastening means. When foot 10 is compressed against the ground, flexion members 11, 14, 20 flex and have a resistance response in which flexed members 11, 14, 20 generate forces resisting such compression.

End 16 is shaped and dimensioned and adapted to be connected to another portion of a leg prosthesis. By way of example, and not limitation, in FIG. 1 a trapezoidal slot 17 is formed in end 16 to receive slidably a tapezoidal finger 18 of an L-shaped member 19 that forms a part of a leg prosthesis. FIG. 7 illustrates an alternate way of shaping an end 16A of a flexible member 14 to facilitate attachment of a prosthetic foot 10A to the lower end of a prosthetic leg, or to a prosthetic device attached to the remaining portion of an individual's leg.

Resilient bottom member 11 includes bottom surface 24 and upper surface 25. Resilient heel member 20 includes upper contact surface 32. Resilient toe member 14 includes lower contact surface 33, and includes ridge 32A. When foot 10 is compressed and member 14 is compressed and displaced downwardly toward member 11, ridge 32A can contact surface 25 and permit the portion of member 14 to the left of ridge 32A in FIG. 2 to continue to be downwardly depressed against member 20 and toward member 11.

Members 11, 14, 20 extend around and partially enclose open volumetric space 23. When foot 10 is compressed to force members 14 and 20 toward member 11, the volume, or size, of space 23 decreases.

As would be appreciated by those of skill in the art, foot 10 can, for aesthetic reasons, be inserted in a hollow, pliable, resilient replica of a foot that is made from rubber, another polymer, or another material. The use of such a housing or some other desired covering for foot 10 ordinarily will not alter the functioning of foot 10 as described below.

The ground, floor, or other surface 30 illustrated in FIGS. 2 to 5 is variously shown as sloped upwardly, sloped downwardly, or level; this to indicate that the foot 10 generally functions in a similar manner on sloped or flat surfaces.

In FIGS. 2 to 5 it is assumed that foot 10 is mounted on the lower end of a prosthetic device, that the prosthetic device and foot 10 are mounted on an amputee or other individual and form at least a portion of an individual's leg, and that the individual is walking and is therefore utilizing the prosthetic device and foot 10 mounted on the lower end thereof.

Figure 2:
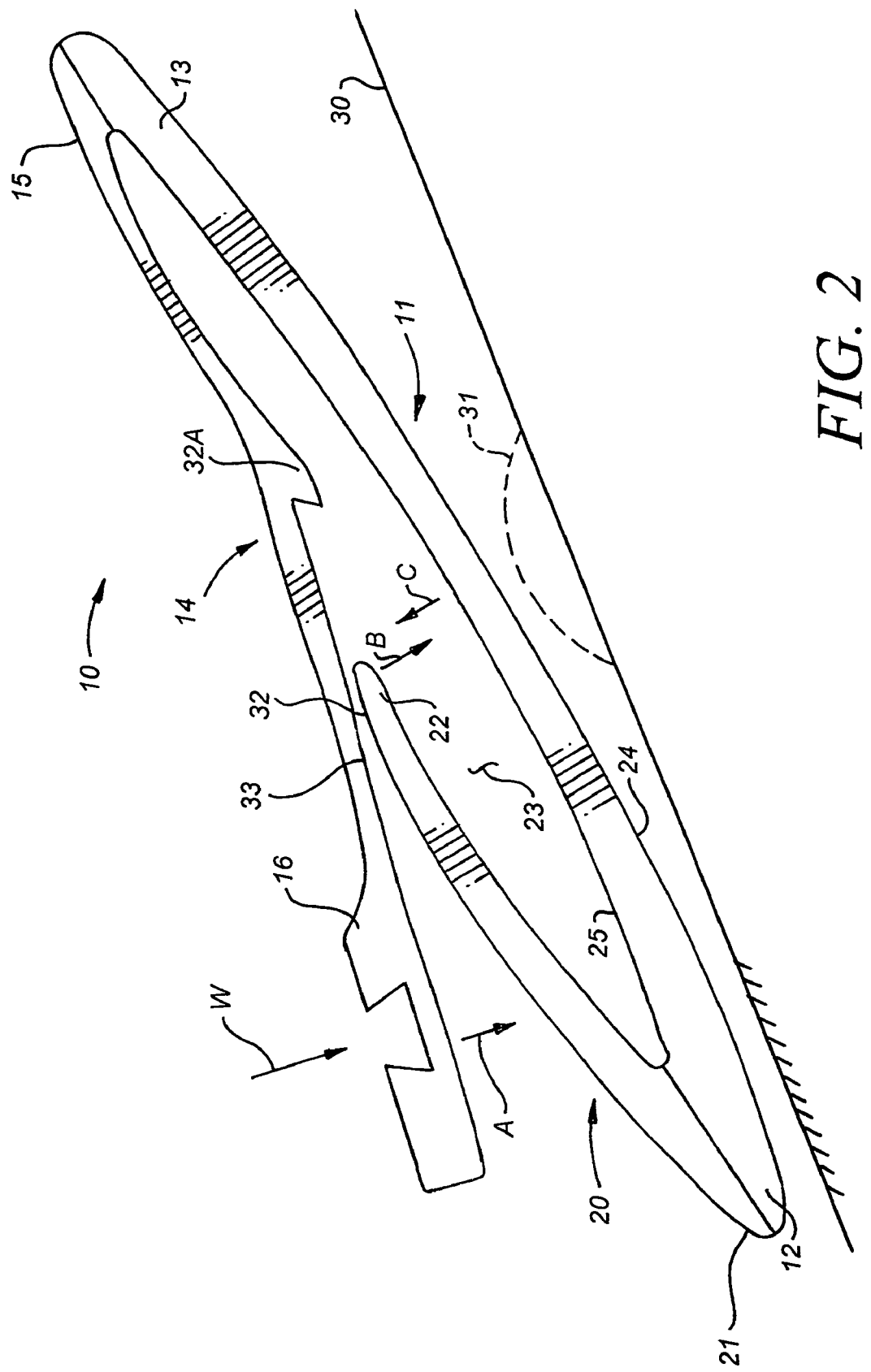
FIG. 2 is a side view further illustrating the prosthetic foot of FIG. 1 prior to impact.

FIG. 2 illustrates foot 10 just prior to heel strike. At heel strike, foot 10 is generally in front of the individual's upper body, as is normally the case when a person is walking.

Figure 3:
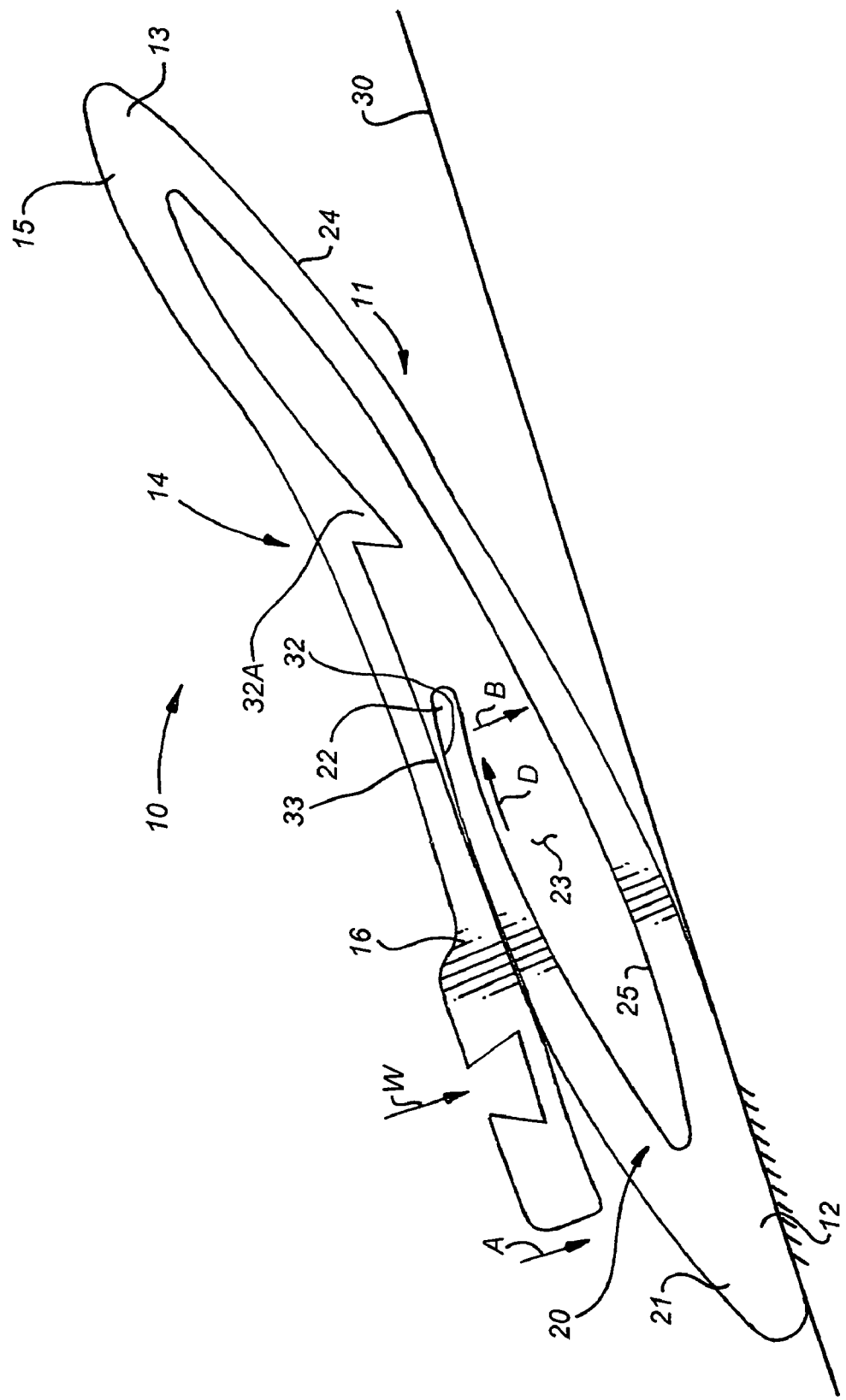
FIG. 3 is a side view illustrating the prosthetic foot of FIG. 1 at the impact of the heel.

FIG. 3 illustrates foot 10 shortly after heel strike. After the bottom surface 24 on end 12 of member 11 contacts the ground 30, the weight, indicated by arrow W in FIGS. 2 to 5, compresses end 16 downwardly in the direction of arrow A in FIGS. 2 and 3 such that surface 33 slidably contacts surface 32 and member 14 forces end 22 of member 20 downwardly in the direction indicated by arrows B in FIGS. 2 and 3. Surface 32 slides over surface 33 in the direction indicated by arrow D in FIG. 3. As the individual continues his stride after heel strike, foot 10 rolls from the heel strike position of FIG. 3 to the mid stance position illustrated in FIG. 4. In the mid stance position, the individual's leg and upper body are generally directly above foot 10 and a larger proportion of the individual's weight bears down on foot 10.

Figure 4:
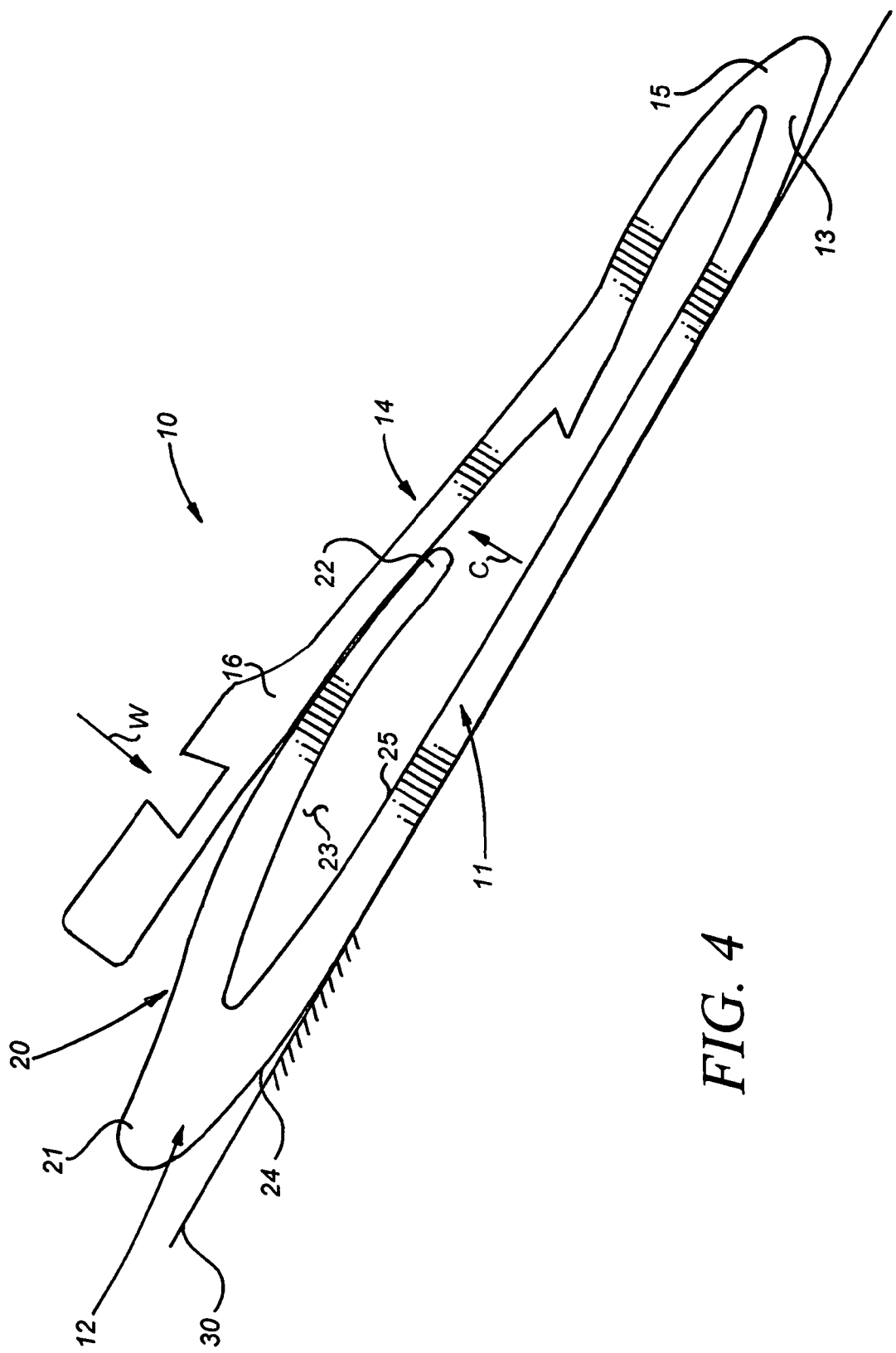
FIG. 4 is a side view illustrating the prosthetic foot of FIG. 1 after it has moved, or rolled, from the heel strike of FIG. 3 to midstance.

When foot 10 rolls over bottom surface 24 from the heel strike position of FIG. 3 to the mid stance position of FIG. 4, the downward displacement and compression of resilient members 14 and 20 continues; however, at the same time bottom member 11 is compressed, member 11 flexes upwardly in the direction of arrow C in FIGS. 2 and 4, and the convex curvature of member 11 flattens. The flattening of member 11 may initiate at, or shortly after heel strike, but the flattening is preferably clearly pronounced at mid stance. As the individual continues his stride after foot 10 reaches mid stance, foot 10 rolls from the mid stance position of FIG. 4 to the toe strike position of FIG. 5.

Figure 5:
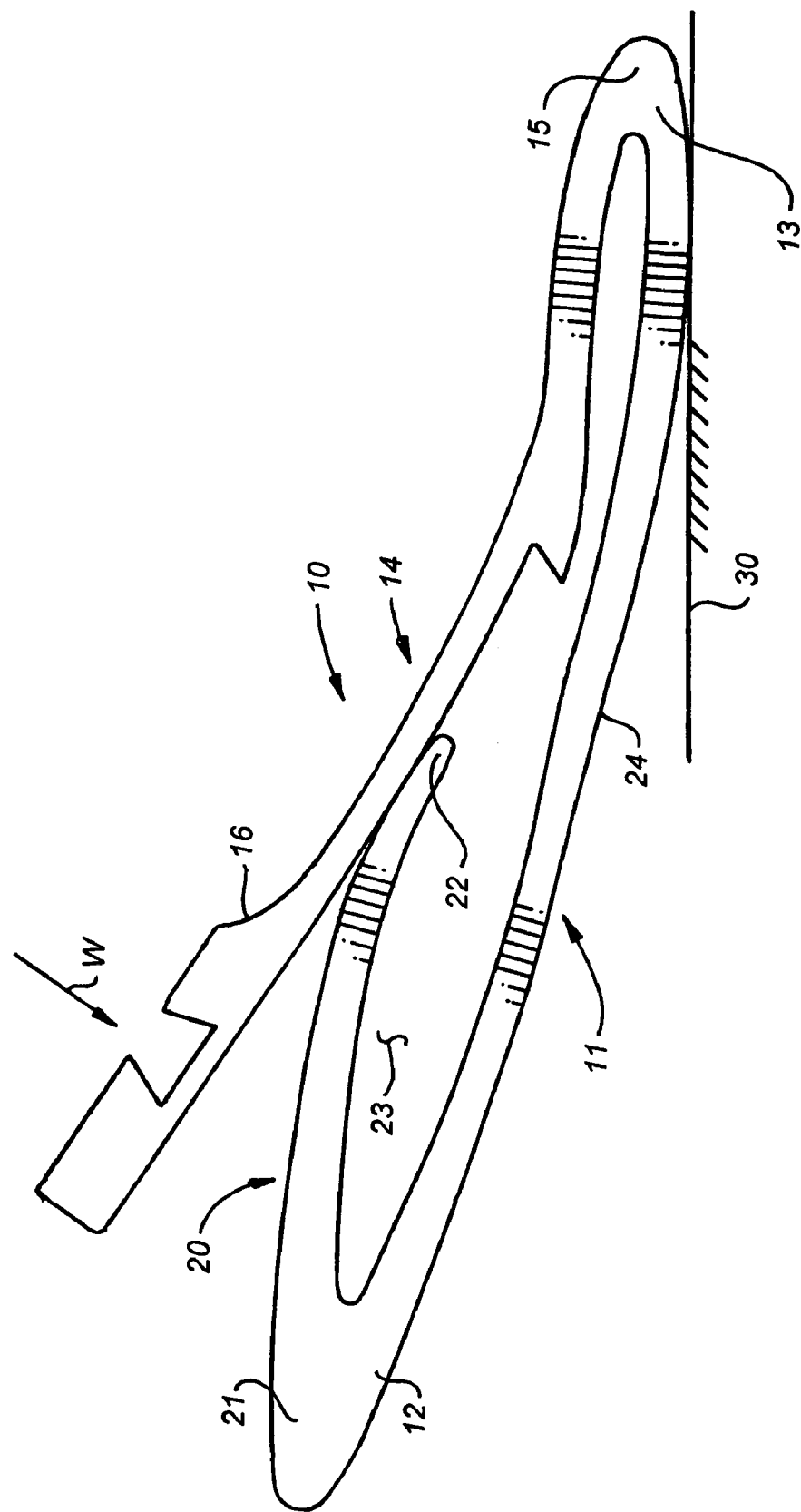
FIG. 5 is a side view illustrating the prosthetic foot of FIG. 1 after it has moved, or rolled, from the midstance of FIG. 4 onto the toe.

When the toe strike position of FIG. 5 is reached, member 11 normally has preferably resiliently returned at least in part to its original convex shape of FIG. 2, and members 14 and 20 have partially returned to their original unflexed position illustrated in FIG. 2. Members 14 and 20 normally, are, however, still partially downwardly compressed and flexed in the manner illustrated in FIG. 5. At toe strike, foot 10 is generally behind the individual's upper body, as is normally the case when a person is walking. As the individual continues his stride, lifts foot 10 off the ground, and put his other foot on the ground, foot 10 regains its unflexed configuration illustrated in FIGS. 1 and 2.

As would be appreciated by those of skill in the art, it is possible to fabricate members 11, 14, 20 such that they are exceedingly stiff and will not resiliently flex at all when an individual wearing a prosthetic device on his leg walks on foot 10. This would, of course, defeat the purpose of the invention. The "stiffness" or resistance to flexure of members 11, 14, 20 can be adjusted as desired; however, the flexure of members 11, 14, 20 is adjusted such that foot 10 will absorb at least a portion of the impact encountered by an individual when foot 10 strikes and rolls over the ground.

Another embodiment of the invention is illustrated in the form of foot 10A in FIGS. 7 and 8. Foot 10A is similar to foot 10 and includes the same resilient bottom member 11. However, in foot 10A resilient heel member 20A is shorter than heel member 20. Resilient member 14A includes an end 15A similar to end 15 of member 14. However, end 16A of member 14A is shaped differently from end 16 and includes an orthogonal tongue 44 that includes an aperture 45 formed therethrough to receive a bolt 41 that secures connector 40 to tongue 44. Connector 40 includes spaced apart legs 42, 43 that slide over the top of tongue 44. Each leg 42, 43 include an aperture formed therethrough that is, when connector 40 is mounted on the top on tongue 44 in the manner illustrated in FIG. 7, in registration with aperture 45 such that bolt 41 can extend through all three apertures to secure connector 40 on tongue 44.

In FIG. 7, a resilient polymer bridge 46 is fixedly secured to the bottom of member 14A (or, if desired, to the top of end 22A) and includes a smooth arcuate outer surface 46A that slides over the upper surface 32A of end 22A when members 14A and 20A are compressed toward member 11 by an individual's weight. Foot 10A functions in substantially the same manner as foot 10.

An another embodiment of the invention, heel member 20, 20A is removed and is not utilized in a foot 10, 10A.

In a further embodiment of the invention, toe member 14, 14A is removed and is not utilized in a foot 10, 10A, in which case end 22A is shaped and dimensioned like end 16, 16A to be attached to a prosthetic leg worn by an individual.

In still another embodiment of the invention, instead of toe member 14, 14A extending upwardly over heel member 20, 20A in the manner illustrated in FIGS. 2 to 5 and 7, foot 10, 10A is shaped and dimensioned such that heel member 20, 20A extends upwardly over toe member 14, 14A—in which case a portion of heel member 20, 20A is shaped to perform the function of end 16 and to attach to a prosthetic leg worn by an individual.

In FIG. 2, end 22 can, if desired, be fixedly secured to member 14, although this is not presently preferred.

Member 11 and space 23 are important features of the invention because they enables foot 10 to roll over and traverse an upraised area 31 on the ground without producing a "kick back" force that tends to force an amputee's leg rearwardly. Member 11 deflects in the direction of arrow C (FIG. 2) to absorb forces produced by upraised area 31.

While it is presently preferred that member 11 have a convex shape and surface 24 in the manner illustrated in FIGS. 1 to 5 and 7, member 11 can still deflect and function to absorb some forces (particularly those forces produced by an upraised member 31) if member 11 is relatively flat in the manner indicated by dashed lines 11A in FIG. 7, or if member 11 is concave in the manner indicated by dashed lines 11B in FIG. 7.

Figure 9:
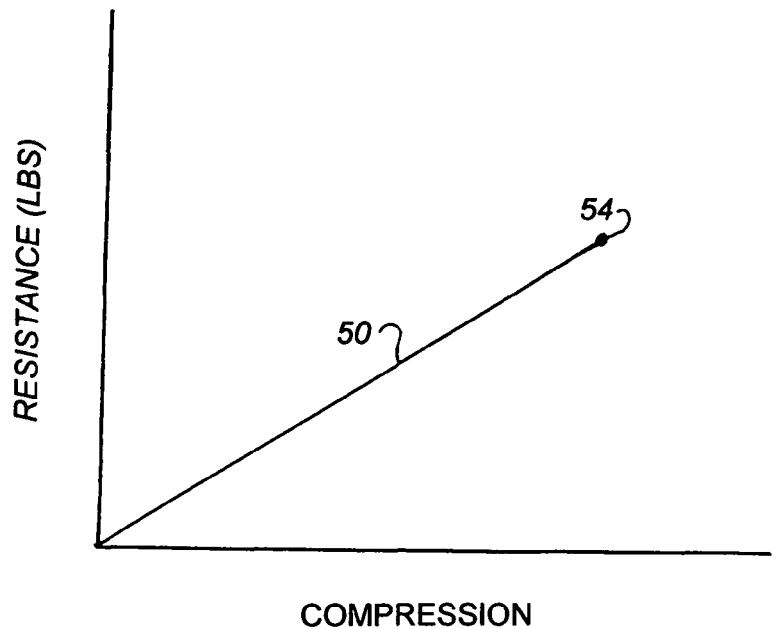
FIG. 9 is a graph generally illustrating the resistance-compression profile of a typical prior art prosthetic foot; and, FIG. 10 is a graph generally illustrating the resistance-compression profile of the prosthetic foot of the invention.
Figure 10:
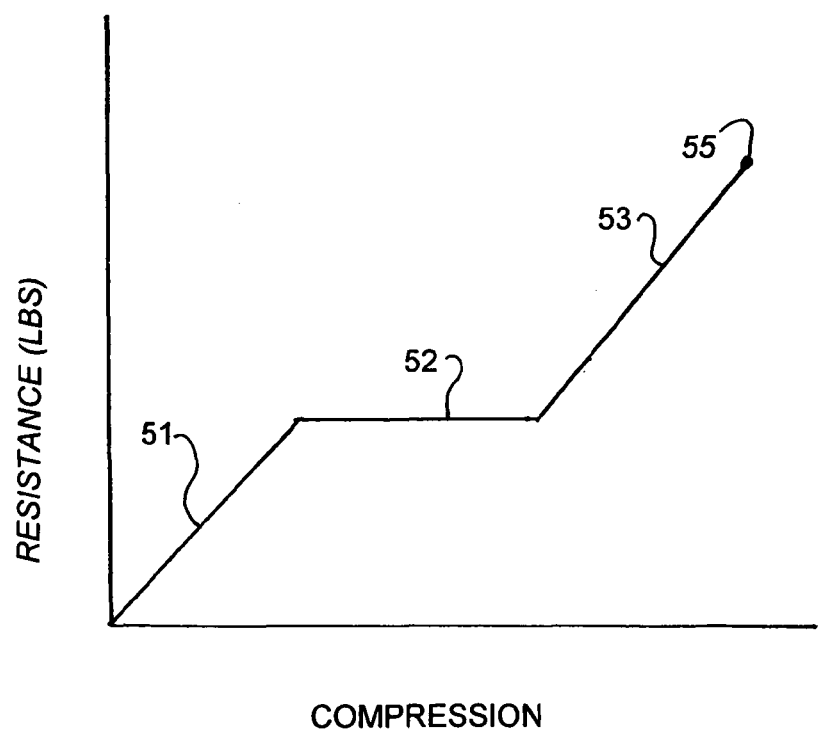

FIG. 9 is a resistance-compression graph generally representing a typical prior art prosthetic foot. As is indicated by line 50 in FIG. 9, when a prior art prosthetic foot is compressed, the resistance response comprises a steadily increasing resistive force up until the prosthetic foot breaks 54. In contrast, the prosthetic foot of the invention has a resistance-compression graph of the general type illustrated in FIG. 10, in which the resistive force increases as indicated by line 51, levels off as indicated by line 52, and then increases as indicated by line 53 up until the prosthetic foot breaks 55. In FIGS. 9 and 10, "compression" on the horizontal axis of each graph indicates the distance that the foot is compressed toward the ground (or other surface) from its normal at rest configuration. The greater the compressive force that is applied to a prosthetic foot, the more the foot is flattened and pressed against the ground or another surface against which the foot is being pressed. In FIGS. 9 and 10, "resistance" in pounds on the vertical axis of each graph indicates the compressive force required to compress the prosthetic foot through the distance indicated on the horizontal axis.

Figure 6:
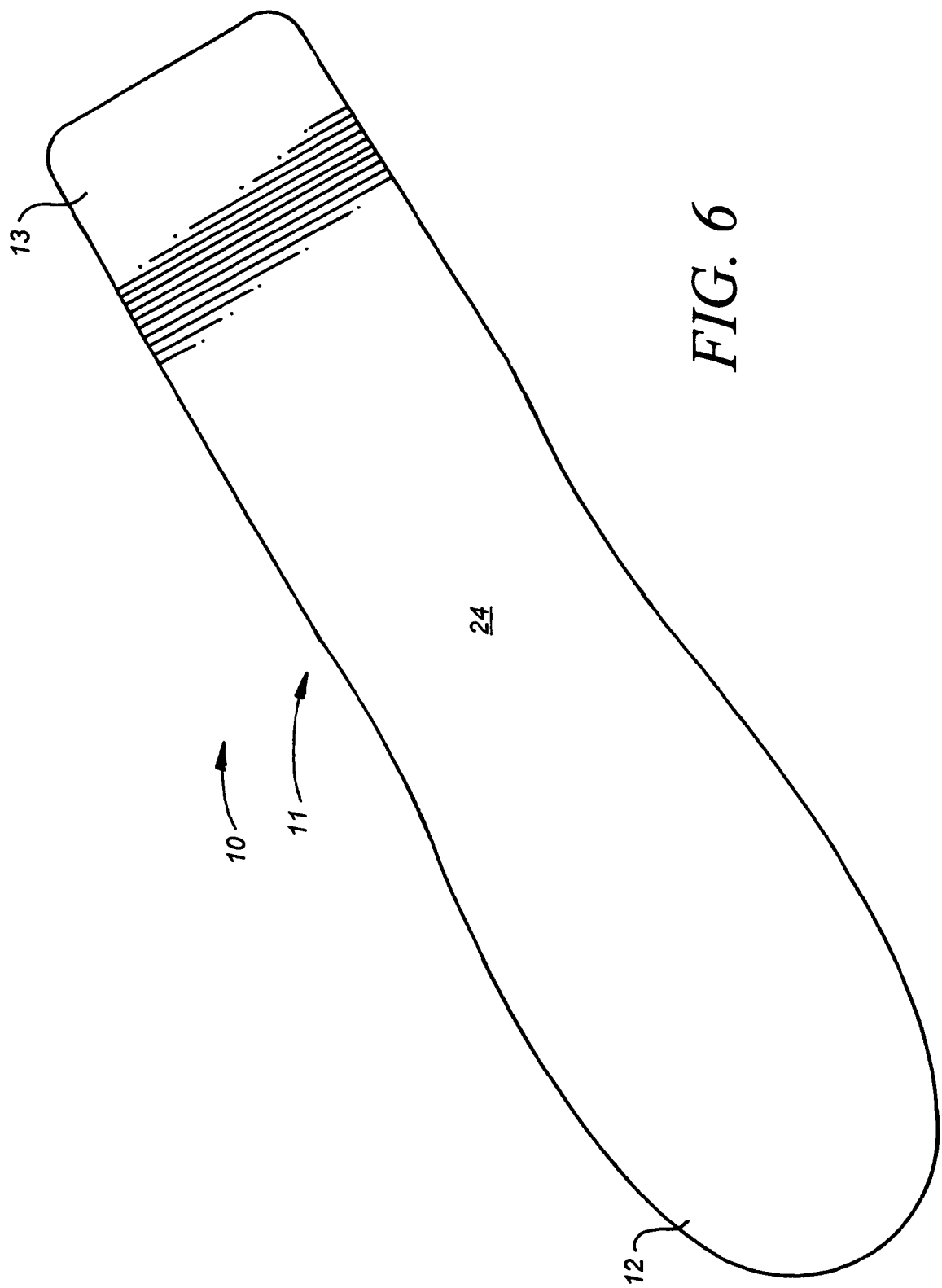
FIG. 6 is a bottom view illustrating the prosthetic foot of FIG. 1.

FIG. 6 is a bottom view of foot 10. If desired, portions of member 11 may be removed to alter the flexure resistance of member 11.

FIG. 8 is a back view of foot 10A. The curvature of bridge 46 can be altered to the configuration indicated by dashed line 47 to better enable bridge 46 to roll in the directions indicated by arrows E and F so that member 14A can laterally twist in the directions indicated by arrows E and F to simulate the inward and outward rotation of a person's ankle.

Having described my invention in such terms as to enable those of skill in the art to make and practice it, and having described the presently preferred embodiments thereof, I claim:

1. A prosthetic foot comprising a unitary member including
   (a) a ground engaging bottom resilient flexion member (11) having
      (i) a front end (13),
      (ii) a back end (12),
      (iii) an intermediate section spanning between and connecting said front end and said back end, and
      (iv) a bottom ground engaging surface (24) extending substantially continuously from said front end to said back end,
      (v) an upper surface (25), and
      (vi) a convex curvature;
   (b) a heel resilient flexion member (20)
      (i) having a rear end (21) connected to said back end (12) of said bottom resilient flexion member (11),
      (ii) extending upwardly from said back end (12) and over said intermediate section toward said front end (13),
      (iii) having a forward end spaced apart from said back end (12) and said bottom resilient flexion member (11), and
      (iv) having a heel contact surface (32) on said forward end;
   (c) a toe resilient flexion member (14)
      (i) having a proximate end (15) connected to said front end (13) of said bottom resilient flexion member (11),
      (ii) extending upwardly from said front end (13), over said intermediate section toward said back end (12), and over said forward end and said heel contact surface (32) of said heel resilient flexion member (20),
      (iii) having a distal end (16) spaced apart from said proximate end (15), spaced apart from said front end (13), spaced above said heel resilient member (20), and
      (iv) including a toe contact surface (33) spaced above said heel contact surface (32), said bottom resilient flexion member, heel resilient flexion member, and toe resilient flexion member being shaped and dimensioned and having a resistance response to a compressive applied force such that when the compressive applied force compresses said prosthetic foot and said bottom resilient flexion member (11) against the ground
   (d) said bottom resilient flexion member (11) flexes upwardly;
   (e) said convex curvature of said bottom resilient flexion member 11 flattens;
   (f) said toe resilient flexion member
      (i) resiliently downwardly deflects toward the ground,
      (ii) contacts said heel resilient flexion member, and
      (iii) deflects said heel resilient flexion member toward the ground and toward said bottom resilient flexion member; and,
   (g) said toe contact surface (33) slides over said heel contact surface (32).

2. The prosthetic foot of claim 1 wherein
   (a) said bottom ground engaging surface is arcuate and convex;
   (b) said toe contact surface (32) is arcuate and convex.

* * * * *